(12) United States Patent  
Alon et al.

(10) Patent No.: US 11,020,585 B2  
(45) Date of Patent: Jun. 1, 2021

(54) TREATING AUTOIMMUNE DISEASES USING AN ALTERNATING ELECTRIC FIELD TO REDUCE THE PROLIFERATION OF T-CELLS

(71) Applicant: Novocure GmbH, Root (CH)

(72) Inventors: Yaniv Alon, Netanya (IL); Tali Voloshin-Sela, Kibbutz Gvat (IL); Moshe Giladi, Moshav Herut (IL)

(73) Assignee: Novocure GmbH, Root (CH)

( * ) Notice: Subject to any disclaimer, the term of this patent is extended or adjusted under 35 U.S.C. 154(b) by 91 days.

(21) Appl. No.: 16/560,134

(22) Filed: Sep. 4, 2019

(65) Prior Publication Data

US 2020/0078582 A1    Mar. 12, 2020

Related U.S. Application Data

(60) Provisional application No. 62/728,174, filed on Sep. 7, 2018.

(51) Int. Cl.
*A61N 1/04*    (2006.01)
*A61N 1/36*    (2006.01)

(52) U.S. Cl.
CPC ......... *A61N 1/0456* (2013.01); *A61N 1/3616* (2013.01)

(58) Field of Classification Search
None
See application file for complete search history.

(56) References Cited

U.S. PATENT DOCUMENTS

| 6,868,289 | B2 | 3/2005  | Palti |
| 7,016,725 | B2 | 3/2006  | Palti |
| 7,089,054 | B2 | 8/2006  | Palti |
| 7,136,699 | B2 | 11/2006 | Palti |
| 7,146,210 | B2 | 12/2006 | Palti |
| 7,333,852 | B2 | 2/2008  | Palti |
| 7,467,011 | B2 | 12/2008 | Palti |
| 7,519,420 | B2 | 4/2009  | Palti |
| 7,565,205 | B2 | 7/2009  | Palti |
| 7,565,206 | B2 | 7/2009  | Palti |
| 7,599,745 | B2 | 10/2009 | Palti |
| 7,599,746 | B2 | 10/2009 | Palti |
| 7,706,890 | B2 | 4/2010  | Palti |
| 7,715,921 | B2 | 5/2010  | Palti |

(Continued)

FOREIGN PATENT DOCUMENTS

JP    2006167476 A    6/2006

OTHER PUBLICATIONS

International Search Report and Written Opinion issued in application No. PCT/IB2019/057452 dated Dec. 9, 2019.

*Primary Examiner* — Brian T Gedeon

(74) *Attorney, Agent, or Firm* — Potomac Law Group, PLLC

(57) ABSTRACT

Damage from autoimmune diseases can be prevented or minimized by positioning a plurality of electrodes in or on a subject's body, and applying an AC voltage between the plurality of electrodes so as to impose an alternating electric field through the tissue that is being attacked by the autoimmune disease and/or draining lymph nodes associated with that tissue. The frequency and field strength of the alternating electric field are selected such that the alternating electric field inhibits proliferation of T cells in the tissue to an extent that reduces damage that is caused by the autoimmune disease.

21 Claims, 1 Drawing Sheet

(56) References Cited

U.S. PATENT DOCUMENTS

| | | |
|---|---|---|
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2005/0075701 A1* | 4/2005 | Shafer .................... A61N 1/326 607/72 |
| 2006/0167499 A1 | 7/2006 | Palti |
| 2007/0239213 A1 | 10/2007 | Palti |
| 2009/0247934 A1* | 10/2009 | Tracey .................... A61P 29/00 604/20 |
| 2012/0283726 A1 | 11/2012 | Palti |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |

* cited by examiner

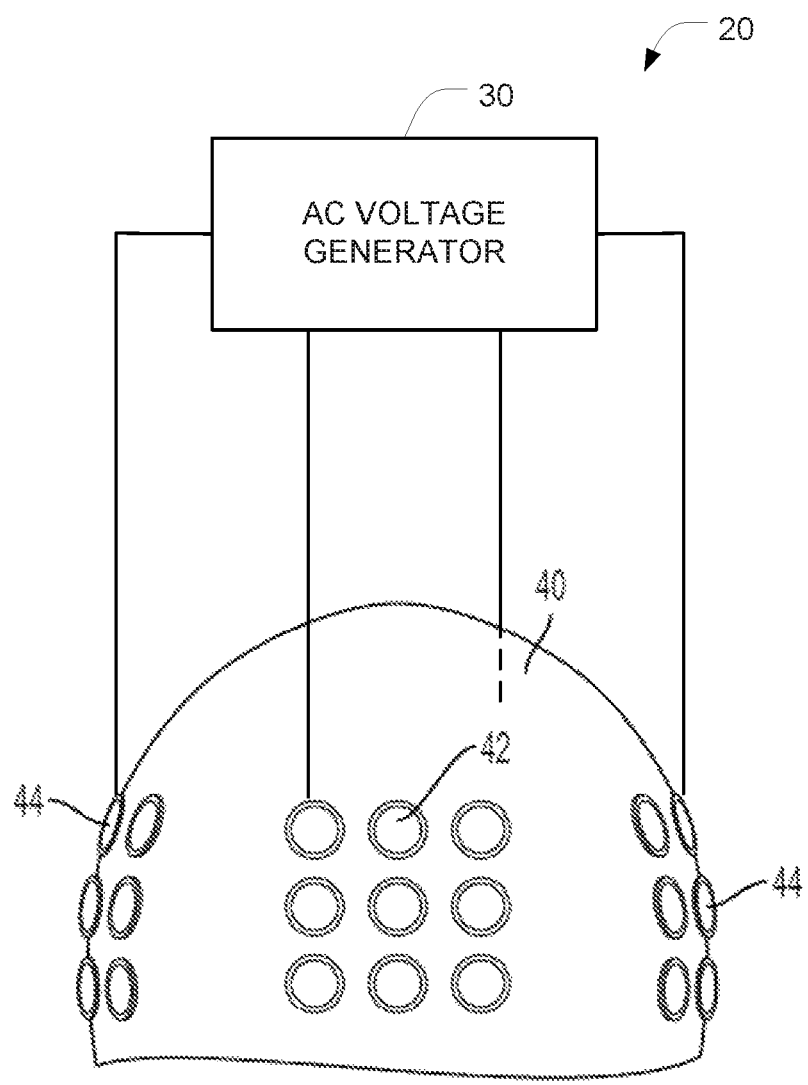

TREATING AUTOIMMUNE DISEASES USING AN ALTERNATING ELECTRIC FIELD TO REDUCE THE PROLIFERATION OF T-CELLS

CROSS REFERENCE TO RELATED APPLICATIONS

This Application claims the benefit of U.S. Provisional Application 62/728,174 filed Sep. 7, 2018, which is incorporated herein by reference in its entirety.

BACKGROUND

In autoimmune diseases, a person's own immune system mistakenly attacks specific portions of the person's body. Examples of T cells dependent autoimmune diseases include: diabetes mellitus type I (where the immune system attacks beta cells in the pancreas); rheumatoid arthritis (where the immune system attacks the synovial membranes of joints); multiple sclerosis (where the immune system attacks the central nervous system); polymyositis (where the immune system attacks certain muscles); lupus nephritis (where the immune system attacks the glomeruli in the kidney); and Rasmussen's encephalitis (where the immune system attacks portions of the brain).

In a separate field, it has been established that tumors (e.g., glioblastoma) can be treated by applying a 200 kHz alternating electric field to the tumor. This is described in U.S. Pat. Nos. 7,016,725 and 7,565,205, each of which is incorporated herein by reference in its entirety. And in the context of treating tumors, these alternating electric fields are referred to as "tumor treating fields" or "TTFields." TTFields are delivered using a wearable and portable device called Optune® made by Novocure™.

SUMMARY OF THE INVENTION

One aspect of the invention is directed to a first method of preventing or minimizing damage from an autoimmune disease in a target region of a subject's body. The first method comprises positioning a plurality of electrodes in or on the subject's body positioned with respect to the target region so that application of an AC voltage between the plurality of electrodes will impose an alternating electric field through tissue that is being attacked by the autoimmune disease in the target region; and applying an AC voltage between the plurality of electrodes for an interval of time, such that an alternating electric field is imposed through the tissue for the interval of time. The alternating electric field has a frequency and a field strength such that when the alternating electric field is imposed in the tissue for the interval of time, the alternating electric field inhibits proliferation of T cells in the tissue to an extent that reduces damage that is caused by the autoimmune disease.

In some instances of the first method, the plurality of electrodes is also positioned with respect to the subject's body so that the alternating electric field is imposed in at least one draining lymph node associated with the tissue that is being attacked.

In some instances of the first method, the autoimmune disease is type 1 diabetes, and the plurality of electrodes is positioned with respect to the subject's body so that the alternating electric field is imposed in a pancreas. In some of these instances, the plurality of electrodes is also positioned with respect to the subject's body so that the alternating electric field is imposed in at least one pancreatic draining lymph node.

In some instances of the first method, the autoimmune disease is multiple sclerosis, and the plurality of electrodes is positioned with respect to the subject's body so that the alternating electric field is imposed in at least one lesion in the subject's central nervous system.

In some instances of the first method, the autoimmune disease is polymyositis, and the plurality of electrodes is positioned with respect to the subject's body so that the alternating electric field is imposed in at least one muscle of the subject. In some of these instances, the plurality of electrodes is also positioned with respect to the subject's body so that the alternating electric field is imposed in at least one draining lymph node associated with the at least one muscle.

In some instances of the first method, the autoimmune disease is rheumatoid arthritis, and the plurality of electrodes is positioned with respect to the subject's body so that the alternating electric field is imposed in at least one joint of the subject. In some of these instances, the plurality of electrodes is also positioned with respect to the subject's body so that the alternating electric field is imposed in at least one draining lymph node associated with the at least one joint.

In some instances of the first method, the autoimmune disease is Rasmussen encephalitis, and the plurality of electrodes is positioned with respect to the subject's body so that the alternating electric field is imposed in an affected hemisphere of the subject's brain.

In some instances of the first method, the autoimmune disease is lupus nephritis, and the plurality of electrodes is positioned with respect to the subject's body so that the alternating electric field is imposed in at least one kidney of the subject. In some of these instances, the plurality of electrodes is also positioned with respect to the subject's body so that the alternating electric field is imposed in at least one draining lymph node associated with the at least one kidney.

In some instances of the first method, the positioning comprises positioning a first set of electrodes in or on the subject's body and positioning a second set of electrodes in or on the subject's body. The first set of electrodes is positioned with respect to the target region so that application of an AC voltage between the electrodes of the first set will impose an alternating electric field with a first orientation through the tissue that is being attacked by the autoimmune disease in the target region. The second set of electrodes is positioned with respect to the target region so that application of an AC voltage between the electrodes of the second set will impose an alternating electric field with a second orientation through the tissue. The first orientation and the second orientation are different. The applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue. The alternating electric field with the first orientation has a frequency and a field strength such that when the alternating electric field with the first orientation is imposed in the tissue, the alternating electric field with the first orientation inhibits proliferation of T cells in the tissue. The alternating electric field with the second orientation has a frequency and a field strength such that when the alternating electric field with the second orientation is imposed in the tissue, the alternating electric field with the second orientation inhibits proliferation of T cells in the tissue. The inhibited proliferation of T cells in the tissue reduces damage that is caused by the autoimmune disease.

Optionally, in the instances of the first method described in the previous paragraph, the first and second sets of electrodes may also be positioned with respect to the subject's body so that the alternating electric fields with the first and second orientations are also imposed in at least one draining lymph node associated with the tissue that is being attacked. Optionally, in the instances of the first method described in the previous paragraph, the first orientation is offset from the second orientation by at least 60°.

Another aspect of the invention is directed to a second method of preventing or minimizing damage from an autoimmune disease in tissue that is being attacked by the autoimmune disease. The second method comprises positioning a plurality of electrodes in or on a subject's body positioned with respect to at least one draining lymph node associated with the tissue that is being attacked so that application of an AC voltage between the plurality of electrodes will impose an alternating electric field through the at least one draining lymph node; and applying an AC voltage between the plurality of electrodes for an interval of time, such that an alternating electric field is imposed through the at least one draining lymph node for the interval of time. The alternating electric field has a frequency and a field strength such that when the alternating electric field is imposed in the at least one draining lymph node for the interval of time, the alternating electric field inhibits proliferation of T cells in the at least one draining lymph node to an extent that reduces damage that is caused by the autoimmune disease.

In some instances of the second method, the positioning comprises positioning a first set of electrodes in or on the subject's body and positioning a second set of electrodes in or on the subject's body. The first set of electrodes is positioned with respect to the at least one draining lymph node associated with the tissue that is being attacked so that application of an AC voltage between the electrodes of the first set will impose an alternating electric field with a first orientation through the at least one draining lymph node, and the second set of electrodes is positioned with respect to the at least one draining lymph node so that application of an AC voltage between the electrodes of the second set will impose an alternating electric field with a second orientation through the at least one draining lymph node. The first orientation and the second orientation are different. The applying comprises repeating, in an alternating sequence, (a) applying a first AC voltage between the electrodes of the first set, such that an alternating electric field with the first orientation is imposed through the at least one draining lymph node and (b) applying a second AC voltage between the electrodes of the second set, such that an alternating electric field with the second orientation is imposed through the at least one draining lymph node. The alternating electric field with the first orientation has a frequency and a field strength such that when the alternating electric field with the first orientation is imposed in the at least one draining lymph node, the alternating electric field with the first orientation inhibits proliferation of T cells in the at least one draining lymph node. The alternating electric field with the second orientation has a frequency and a field strength such that when the alternating electric field with the second orientation is imposed in the at least one draining lymph node, the alternating electric field with the second orientation inhibits proliferation of T cells in the at least one draining lymph node. The inhibited proliferation of T cells in the at least one draining lymph node reduces damage that is caused by the autoimmune disease.

Optionally, in the instances of the second method described in the previous paragraph, the first orientation is offset from the second orientation by at least 60°.

Optionally, in any of the instances of the first or second methods described above, each of the plurality of electrodes is capacitively coupled to the subject's body. Optionally, in any of the instances of the first or second methods described above, the positioning and the applying are implemented after it has been determined that an acute phase of the autoimmune disease is starting.

Optionally, any of the instances of the first or second methods described above further comprise treating the autoimmune disease with a therapeutically effective drug regimen.

Optionally, in any of the instances of the first or second methods described above, the alternating electric field has a frequency of about 200 kHz. Optionally, in any of the instances of the first or second methods described above, the alternating electric field has a frequency between 50 and 500 kHz. Optionally, in any of the instances of the first or second methods described above, the alternating electric field has a field strength between 1 and 5 V/cm RMS. Optionally, in any of the instances of the first or second methods described above, the tissue is tumor-free.

BRIEF DESCRIPTION OF THE DRAWINGS

FIG. 1 is a schematic representation of a system for applying alternating electric fields to tissue in a person's brain that is used to minimize damage to brain tissue caused by an autoimmune disease.

Various embodiments are described in detail below with reference to the accompanying drawings, wherein like reference numerals represent like elements.

DESCRIPTION OF THE PREFERRED EMBODIMENTS

In the embodiments described below, a system that is similar to the Optune® system for treating tumors with TTFields is used to treat an autoimmune disease instead of treating a tumor. Although use of the Optune® system for treating glioblastoma is well-understood by persons skilled in the relevant arts, it will be described here briefly for completeness. Four arrays of capacitively coupled electrodes (also called "transducer arrays") are positioned on the subject' shaved head (e.g., one on the front, one on the back, one on the right side, and one on the left side). An AC voltage generator applies an AC voltage at 200 kHz between the front/back pair of electrode arrays for one second, then applies an AC voltage at the same frequency between the right/left pair of electrode arrays for one second, and repeats this two-step sequence for the duration of the treatment. This induces TTFields in the first and second orientations through the subject's brain in an alternating sequence. The electrode arrays are positioned so that the first orientation and the second direction are offset by a significant amount (e.g., at least 60°, or at least 80°).

T cells in the body's immune system can play a very important role in combating tumors. In view of this, studies were done to ascertain whether TTFields might interfere with the operation of T cells. One such study concluded that "As the presence of polyfunctional T cells is associated with effective anti-tumoral responses, a single-cell level polyfunctionality analysis of activated T cells was performed. The analysis demonstrated that under TTFields conditions non proliferating cells retained all other combinations of immune functions. TTFields were found to have a minor effect on the viability of un-activated T cells. In activated cells, there was a moderate effect on cells that did not attempt to proliferate, but TTFields substantially reduced the viability rate of cells that had proliferated. These findings were true for both helper and cytotoxic T cells." Evaluating the In-Vitro Effects of Tumor Treating Fields on T Cell Responses, G. Diamant et al., Proceedings of the AACR, Volume 58, Abstract #617, April 2017.

In the context of treating tumors, because fewer T cells will be available to attack the tumor cells, reducing the proliferation of T cells is a drawback. But in the context of treating an autoimmune disease, this very same drawback is advantageously transformed into a benefit. More specifically, this application explains how autoimmune diseases can be treated by using an alternating electric field ("AEF") to inhibit the proliferation of T cells, which are key participants in the immune system's attack on a person's body. Because AEFs can inhibit the proliferation of T cells, AEFs can prevent or reduce the damage that T cells inflict on a person's body in the context of an autoimmune disease, which can slow the progression of the disease.

Furthermore, many autoimmune diseases have distinct stages during which the immune system attacks tissue in a subject's body. For these autoimmune diseases, the application of the AEFs may be timed to coincide with the intervals of time during which the immune system is actively attacking the relevant tissue. In many preferred embodiments, the electrodes are positioned to maximize the electric field in the tissue that is being attacked by the immune system. The concepts described herein are applicable to a wide variety of autoimmune diseases, including but not limited to the diseases identified individually below.

In type 1 diabetes, the immune system damages the beta cells of the pancreas in stage 1 (where the subjects are still normal glycemic) and stage 2 (dysglycemia from loss of functional beta cell mass), so the AEFs should be applied to the relevant anatomy during those stages of the disease to slow the disease's progression. But once type 1 diabetes has progressed to stage 3, the subject's beta cells have already been damaged beyond repair, so there is no point in continuing treatment. Because the immune system is attacking the pancreas, the best positioning for the electrodes is to place one pair of electrodes on the subject's body in front of and behind the pancreas and/or the pancreatic draining lymph nodes, and the second pair of electrodes on the sides of the subject's body at a height that corresponds to the pancreas and/or the pancreatic draining lymph nodes.

In multiple sclerosis (MS), the immune system attacks myelinated axons in the central nervous system. With this disease, the AEFs should be applied to the relevant anatomy of subjects who have been diagnosed with secondary progressive MS, primary progressive MS, relapsing-remitting MS, or progressive relapsing MS to slow the disease's progression. As for positioning of the electrodes, because it may be impractical to apply AEFs to the entire central nervous system, lesions in the CNS may be detected using MRI, and the AEFs may be imposed only in those regions where the lesions were detected. Alternatively, the AEFs could be applied continuously to the subject's scalp as a prophylactic measure to prevent formation of brain lesions.

In polymyositis (PM), the immune system attacks a person's muscles, especially the muscles of the hips, thighs, upper arms, shoulder, neck, and the top part of the back. With this disease, the AEFs should be applied to the regions noted above and/or to associated draining lymph nodes to slow the disease's progression. For this disease, the electrodes may be positioned along strip-shaped regions that run in a proximal-to-distal direction along the body parts noted above, e.g., with one pair of electrodes positioned in front of and in back of the relevant body part, and a second pair of electrodes positioned on the right and left sides of the relevant body part.

In rheumatoid arthritis (RA), the immune system attacks a person's joints (e.g. knees, hips, shoulders, elbows, wrists, ankles, etc.). With this disease, the AEFs should be applied in subjects who have been diagnosed with polycyclic or progressive RA to the regions noted above and/or to associated draining lymph nodes to slow the disease's progression. The electrodes should be positioned in the vicinity of the joints during active disease and as a prophylactic measure during remission period in polycyclic RA. Note that the electrode positioning configurations disclosed in US 2018/0001075, which is incorporated herein by reference in its entirety, may be used to apply the AEFs to certain joints (e.g. knees, elbows, and wrists).

In Rasmussen encephalitis (RE), the immune system attacks a single hemisphere of a person's brain. This disease typically progresses through three stages: the prodromal stage, the acute stage, and the residual stage. With this disease, the AEFs should be applied to the affected hemisphere of the brain of subjects who had been diagnosed with the acute stage of RE to slow the progression of the disease. Once the disease has progressed to the residual stage, treatment may be discontinued. The electrodes should be positioned on the subject's scalp in order to maximize the field in the affected hemisphere. Many of the approaches for determining the optimal placement of the electrodes in the context of glioblastoma may be used in the context of RE.

In lupus nephritis the immune system attacks a person's kidneys. The best positioning for the electrodes for this disease is to place one pair of electrodes on the subject's body in front of and behind the kidneys and/or associated draining lymph nodes, and the second pair of electrodes on the sides of the subject's body at a height that corresponds to the kidneys and/or the associated draining lymph nodes.

For any of the diseases described above, it is preferable to treat the afflicted portions of the subject's body with AEFs for significant durations of time (e.g., at least 75% of the time, which comes to at least 18 hours a day).

Many autoimmune diseases, including some of the diseases identified above, affect portions of the body (e.g., pancreas, kidneys, etc.) that have associated draining lymph nodes. As most T cell proliferation takes place in the draining lymph nodes, treatment of these autoimmune disease using AEFs may be accomplished by either (a) applying the AEF's to the relevant body part alone (e.g., pancreas, kidneys, etc.) (b) applying the AEF's to the associated draining lymph node or nodes alone; or (c) applying the AEFs to both the relevant body part and the associated draining lymph node or nodes. The decision as to which lymph node or nodes are associated with the relevant body part may be based upon the literature (i.e., in situations where the association between a body part and a specific lymph node is known in medical literature) or personalized to each individual subject using imaging (e.g., CT, MRI, ultrasound, etc.).

FIG. 1 depicts an example system 20 for applying AEFs to tissue in a person's brain that is used to minimize damage to brain tissue caused by an autoimmune disease (e.g., Rasmussen encephalitis). The system 20 includes an AC voltage generator 30, a first set of electrodes 44 positioned on the right and left side of the head, and a second set of electrodes 42 positioned on the front and back of the head. (Because FIG. 1 depicts the front view of the scalp 40, the electrodes 42 that are positioned on the back of the head are not visible in this view.) In the illustrated embodiment, each of the electrodes 42, 44 includes nine circular elements that are wired in parallel. But in alternative embodiments, a different number of elements and/or elements with different shapes may be used, depending on the anatomical location where the electrodes will be positioned for any given autoimmune disease.

To use this system, the first set of electrodes 44 is applied to the subject's body (i.e., on the right and left sides of the head in the illustrated embodiment). The first set of electrodes 44 is positioned with respect to the target region so that application of an AC voltage between the electrodes 44 will impose an alternating electric field with a first orientation (i.e., right to left in the illustrated embodiment) through tissue that is being attacked by the autoimmune disease in the target region (i.e., the brain in the illustrated embodiment). The second set of electrodes 42 is also applied to the subject's body (i.e., on the front and back of the head in the illustrated embodiment). The second set of electrodes is positioned with respect to the target region so that application of an AC voltage between the electrodes 42 will impose an alternating electric field with a second orientation through the tissue (i.e., front to back in the illustrated embodiment). The first orientation and the second orientation are different (and are roughly perpendicular in the illustrated embodiment).

After the first and second set of electrodes 42, 44 have been applied to the subject's body, the AC voltage generator 30 repeats the following steps in an alternating sequence: (a) applying a first AC voltage between the electrodes of the first set 44, such that an alternating electric field with the first orientation is imposed through the tissue and (b) applying a second AC voltage between the electrodes of the second set 42, such that an alternating electric field with the second orientation is imposed through the tissue. The alternating electric field with the first orientation has a frequency and a field strength such that when the alternating electric field with the first orientation is imposed in the tissue, the alternating electric field with the first orientation inhibits proliferation of T cells in the tissue. And the alternating electric field with the second orientation has a frequency and a field strength such that when the alternating electric field with the second orientation is imposed in the tissue, the alternating electric field with the second orientation inhibits proliferation of T cells in the tissue. The inhibition of the proliferation of T cells in the tissue reduces damage that is caused by the autoimmune disease.

In some embodiments, all the electrodes are positioned on the subject's body (as depicted in FIG. 1); in other embodiments, all the electrodes may be implanted in the subject's body (e.g., just beneath the subject's skin, or in the vicinity of the organ being treated); and in other embodiments, some of the electrodes are positioned on the subject's skin and the rest of the electrodes are implanted in the subject's body.

The same frequency that is used in the Optune® system to treat glioblastoma (i.e., 200 kHz) may also be used to treat an autoimmune disease by inhibiting the proliferation of T cells, as described above. But in alternative embodiments, a different frequency may be used. For example, the frequency of the AEFs that are used to treat autoimmune diseases may be between 100 and 300 kHz, between 50 and 500 kHz, or between 25 kHz and 1 MHz. The optimal frequency may be determined experimentally for each individual autoimmune disease. Preferably, care is taken to ensure that the AEFs at the selected frequency do not adversely heat portions of the subject's body.

The field strength of the AEFs may be between 0.2 and 1 V/cm RMS, between 1 and 5 V/cm RMS, or between 5 and 25 V/cm RMS. The optimal field strength may be determined experimentally for each individual autoimmune disease. Here again, care is preferably taken to ensure that the AEFs at the field strength that is being used do not adversely heat portions of the subject's body.

The orientation of the AEFs may be switched at one second intervals between two different orientations by applying AC voltages between two different sets of electrodes, as done in the Optune® system. But in alternative embodiments, the orientation of the AEFs can be switched at a faster rate (e.g., at intervals between 1 and 1000 ms) or at a slower rate (e.g., at intervals between 1 and 100 seconds). In other alternative embodiments, the electrodes need not be arranged in pairs. See, for example, the electrode positioning described in U.S. Pat. No. 7,565,205, which is incorporated herein by reference. In other alternative embodiments, the orientation of the field need not be switched at all, in which case only a single pair of electrodes is required.

In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body.

Optionally, thermal sensors (not shown) may be included at the electrodes, and the AC voltage generator 30 can be configured to decrease the amplitude of the AC voltages that are applied to the electrodes if the sensed temperature at the electrodes gets too high.

In some embodiments, one or more additional pairs of electrodes may be added and included in the sequence. In other embodiments, the field is only imposed in the target region with a single orientation, in which case the alternating sequence described above may be replaced with a continuous AC signal that is applied to a single set of electrodes (e.g., positioned on opposite sides of the target region).

Note that while FIG. 1 depicts an embodiment in which the AEFs are applied to the brain, the AEFs may be applied to different portions of a subject's body as described above in alternative embodiments.

The AEFs may be used to treat an autoimmune disease in tissue (e.g., the brain of a first person with RE) that is tumor free. Alternatively, the AEFs may be used to treat an autoimmune disease in tissue that contains a tumor (e.g., the brain of a different person with both RE and a glioblastoma).

Finally, AEF-based autoimmune therapy may optionally be combined with conventional drugs that are used to treat the respective disease.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of preventing or minimizing damage from an autoimmune disease in a target region of a subject's body, the method comprising:
    positioning a plurality of electrodes in or on the subject's body, positioned with respect to the target region so that application of an AC voltage between the plurality of electrodes will impose an alternating electric field through tissue that is being attacked by the autoimmune disease in the target region; and
    applying an AC voltage between the plurality of electrodes for an interval of time, such that an alternating electric field is imposed through the tissue for the interval of time,
    wherein the alternating electric field has a frequency and a field strength such that when the alternating electric field is imposed in the tissue for the interval of time, the alternating electric field inhibits proliferation of T cells in the tissue to an extent that reduces damage that is caused by the autoimmune disease.

2. The method of claim 1, wherein the plurality of electrodes is also positioned with respect to the subject's body so that the alternating electric field is imposed in at least one draining lymph node associated with the tissue that is being attacked.

3. The method of claim 1, wherein the autoimmune disease is type 1 diabetes, and wherein the plurality of electrodes is positioned with respect to the subject's body so that the alternating electric field is imposed in a pancreas.

4. The method of claim 1, wherein the autoimmune disease is multiple sclerosis, and wherein the plurality of electrodes is positioned with respect to the subject's body so that the alternating electric field is imposed in at least one lesion in the subject's central nervous system.

5. The method of claim 1, wherein the autoimmune disease is polymyositis, and wherein the plurality of electrodes is positioned with respect to the subject's body so that the alternating electric field is imposed in at least one muscle of the subject.

6. The method of claim 1, wherein the autoimmune disease is rheumatoid arthritis, and wherein the plurality of electrodes is positioned with respect to the subject's body so that the alternating electric field is imposed in at least one joint of the subject.

7. The method of claim 1, wherein the autoimmune disease is Rasmussen encephalitis, and wherein the plurality of electrodes is positioned with respect to the subject's body so that the alternating electric field is imposed in an affected hemisphere of the subject's brain.

8. The method of claim 1, wherein the autoimmune disease is lupus nephritis, and wherein the plurality of electrodes is positioned with respect to the subject's body so that the alternating electric field is imposed in at least one kidney of the subject.

9. The method of claim 1,
    wherein the positioning comprises
        positioning a first set of electrodes in or on the subject's body, wherein the first set of electrodes is positioned with respect to the target region so that application of an AC voltage between the electrodes of the first set will impose an alternating electric field with a first orientation through the tissue that is being attacked by the autoimmune disease in the target region, and
        positioning a second set of electrodes in or on the subject's body, wherein the second set of electrodes is positioned with respect to the target region so that application of an AC voltage between the electrodes of the second set will impose an alternating electric field with a second orientation through the tissue, wherein the first orientation and the second orientation are different,
    wherein the applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue,
    wherein the alternating electric field with the first orientation has a frequency and a field strength such that when the alternating electric field with the first orientation is imposed in the tissue, the alternating electric field with the first orientation inhibits proliferation of T cells in the tissue,
    wherein the alternating electric field with the second orientation has a frequency and a field strength such that when the alternating electric field with the second orientation is imposed in the tissue, the alternating electric field with the second orientation inhibits proliferation of T cells in the tissue, and
    wherein the inhibited proliferation of T cells in the tissue reduces damage that is caused by the autoimmune disease.

10. The method of claim 9, wherein the first and second sets of electrodes are also positioned with respect to the subject's body so that the alternating electric fields with the first and second orientations are also imposed in at least one draining lymph node associated with the tissue that is being attacked.

11. The method of claim 9, wherein the first orientation is offset from the second orientation by at least 60°.

12. The method of claim 1, wherein the positioning and the applying are implemented after it has been determined that an acute phase of the autoimmune disease is starting.

13. The method of claim 1, further comprising treating the autoimmune disease with a therapeutically effective drug regimen.

14. The method of claim 1, wherein the alternating electric field has a frequency between 50 and 500 kHz.

15. The method of claim 1, wherein the tissue is tumor-free.

16. A method of preventing or minimizing damage from an autoimmune disease in tissue that is being attacked by the autoimmune disease, the method comprising:
    positioning a plurality of electrodes in or on a subject's body, positioned with respect to at least one draining lymph node associated with the tissue that is being attacked so that application of an AC voltage between the plurality of electrodes will impose an alternating electric field through the at least one draining lymph node; and
    applying an AC voltage between the plurality of electrodes for an interval of time, such that an alternating electric field is imposed through the at least one draining lymph node for the interval of time,
    wherein the alternating electric field has a frequency and a field strength such that when the alternating electric field is imposed in the at least one draining lymph node for the interval of time, the alternating electric field inhibits proliferation of T cells in the at least one draining lymph node to an extent that reduces damage that is caused by the autoimmune disease.

17. The method of claim 16,
wherein the positioning comprises
- positioning a first set of electrodes in or on the subject's body, wherein the first set of electrodes is positioned with respect to the at least one draining lymph node associated with the tissue that is being attacked so that application of an AC voltage between the electrodes of the first set will impose an alternating electric field with a first orientation through the at least one draining lymph node, and
- positioning a second set of electrodes in or on the subject's body, wherein the second set of electrodes is positioned with respect to the at least one draining lymph node so that application of an AC voltage between the electrodes of the second set will impose an alternating electric field with a second orientation through the at least one draining lymph node, wherein the first orientation and the second orientation are different, wherein the applying comprises repeating, in an alternating sequence, (a) applying a first AC voltage between the electrodes of the first set, such that an alternating electric field with the first orientation is imposed through the at least one draining lymph node and (b) applying a second AC voltage between the electrodes of the second set, such that an alternating electric field with the second orientation is imposed through the at least one draining lymph node, wherein the alternating electric field with the first orientation has a frequency and a field strength such that when the alternating electric field with the first orientation is imposed in the at least one draining lymph node, the alternating electric field with the first orientation inhibits proliferation of T cells in the at least one draining lymph node, wherein the alternating electric field with the second orientation has a frequency and a field strength such that when the alternating electric field with the second orientation is imposed in the at least one draining lymph node, the alternating electric field with the second orientation inhibits proliferation of T cells in the at least one draining lymph node, and wherein the inhibited proliferation of T cells in the at least one draining lymph node reduces damage that is caused by the autoimmune disease.

18. The method of claim 16, wherein the positioning and the applying are implemented after it has been determined that an acute phase of the autoimmune disease is starting.

19. The method of claim 16, further comprising treating the autoimmune disease with a therapeutically effective drug regimen.

20. The method of claim 16, wherein the alternating electric field has a frequency between 50 and 500 kHz.

21. The method of claim 16, wherein the tissue is tumor-free.

* * * * *